(12) United States Patent
Song et al.

(10) Patent No.: US 11,116,703 B2
(45) Date of Patent: *Sep. 14, 2021

(54) COMPACT SHAMPOO COMPOSITION CONTAINING SULFATE-FREE SURFACTANTS

(71) Applicant: The Procter & Gamble Company, Cincinnati, OH (US)

(72) Inventors: Brian Xiaoqing Song, Mason, OH (US); Ioannis Constantine Constantinides, Wyoming, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/156,038

(22) Filed: Oct. 10, 2018

(65) Prior Publication Data

US 2019/0105243 A1    Apr. 11, 2019

Related U.S. Application Data

(60) Provisional application No. 62/570,375, filed on Oct. 10, 2017.

(51) Int. Cl.
| | | |
|---|---|---|
| *A61K 8/04* | (2006.01) | |
| *A61K 8/44* | (2006.01) | |
| *A61K 8/46* | (2006.01) | |
| *A61Q 5/02* | (2006.01) | |
| *A61Q 5/00* | (2006.01) | |

(Continued)

(52) U.S. Cl.
CPC ............... *A61K 8/046* (2013.01); *A61K 8/44* (2013.01); *A61K 8/442* (2013.01); *A61K 8/466* (2013.01); *A61K 8/89* (2013.01); *A61Q 5/006* (2013.01); *A61Q 5/02* (2013.01); *A61Q 5/12* (2013.01); *A61K 2800/30* (2013.01); *A61K 2800/596* (2013.01); *A61K 2800/87* (2013.01)

(58) Field of Classification Search
None
See application file for complete search history.

(56) References Cited

U.S. PATENT DOCUMENTS

| | | |
|---|---|---|
| 2,879,231 A | 3/1959 | Allen |
| 3,709,437 A | 1/1973 | Wright |

(Continued)

FOREIGN PATENT DOCUMENTS

| | | |
|---|---|---|
| CA | 2078375 A1 | 3/1994 |
| CN | 102895151 A | 1/2013 |

(Continued)

OTHER PUBLICATIONS

U.S. Appl. No. 16/170,516, filed Oct. 25, 2018, Chang et al.

(Continued)

*Primary Examiner* — Kyung S Chang
(74) *Attorney, Agent, or Firm* — Alexandra S. Anoff

(57) ABSTRACT

A compact shampoo composition containing a cationic polymer and from about 20% to about 40%, by weight, of a surfactant system. The shampoo composition is substantially free of sulfate-based surfactants. The surfactant system contains acyl glutamate, sodium cocoyl isethionate, and a zwitterionic surfactant. The weight ratio of zwitterionic surfactant to sodium cocoyl isethionate can be greater than 1.5.

9 Claims, 1 Drawing Sheet

(51) Int. Cl.
*A61Q 5/12* (2006.01)
*A61K 8/89* (2006.01)

(56) References Cited

U.S. PATENT DOCUMENTS

| | | | |
|---|---|---|---|
| 3,950,532 A | 4/1976 | Bouillon et al. |
| 3,959,160 A | 5/1976 | Horsler et al. |
| 4,309,119 A | 1/1982 | Wittersheim |
| 4,329,334 A | 5/1982 | Su et al. |
| 4,726,945 A | 2/1988 | Patel |
| 4,839,166 A | 6/1989 | Grollier et al. |
| 4,867,971 A | 9/1989 | Ryan et al. |
| 4,997,641 A | 3/1991 | Hartnett |
| 5,294,644 A | 3/1994 | Login et al. |
| 5,332,569 A | 7/1994 | Wood et al. |
| 5,364,031 A | 11/1994 | Taniguchi et al. |
| 5,374,421 A | 12/1994 | Tashiro |
| 5,409,695 A | 4/1995 | Abrutyn et al. |
| 5,415,810 A | 5/1995 | Lee et al. |
| 5,417,965 A | 5/1995 | Janchitraponvej et al. |
| 5,439,682 A | 8/1995 | Wivell |
| 5,441,659 A | 8/1995 | Minor |
| 5,560,918 A | 10/1996 | Wivell |
| 5,578,298 A | 11/1996 | Berthiaume |
| 5,599,549 A | 2/1997 | Wivell |
| 5,624,666 A | 4/1997 | Coffindaffer et al. |
| 5,635,469 A | 6/1997 | Fowler et al. |
| 5,747,436 A | 5/1998 | Patel et al. |
| 5,776,444 A | 7/1998 | Birtwistle et al. |
| 5,816,446 A | 10/1998 | Steindorf et al. |
| 5,830,440 A | 11/1998 | Sturla et al. |
| 5,853,618 A | 12/1998 | Barker |
| 5,902,225 A | 5/1999 | Monson |
| 5,925,603 A | 7/1999 | Angelo |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,153,569 A | 11/2000 | Halloran |
| 6,162,834 A | 12/2000 | Sebillotte-Arnaud et al. |
| 6,231,844 B1 | 5/2001 | Nambu |
| 6,268,431 B1 | 7/2001 | Snyder et al. |
| 6,284,225 B1 | 9/2001 | Bhatt |
| 6,329,331 B1 | 12/2001 | Aronson et al. |
| 6,335,312 B1 | 1/2002 | Coffindaffer et al. |
| 6,423,305 B1 | 7/2002 | Cauwet-Martin et al. |
| 6,451,300 B1 | 9/2002 | Dunlop et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,716,455 B2 | 4/2004 | Birkel |
| 6,743,760 B1 | 6/2004 | Hardy et al. |
| 6,827,795 B1 | 12/2004 | Kasturi et al. |
| 6,897,253 B2 | 5/2005 | Schmucker-castner |
| 6,930,078 B2 | 8/2005 | Wells |
| 6,992,054 B2 | 1/2006 | Lee et al. |
| 7,217,752 B2 | 5/2007 | Schmucker-Castner et al. |
| 7,220,408 B2 | 5/2007 | Decoster et al. |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,928,053 B2 | 4/2011 | Hecht et al. |
| 7,977,288 B2 | 7/2011 | SenGupta |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,300,949 B2 | 10/2012 | Harichian et al. |
| 8,343,469 B2 | 1/2013 | Bierganns et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,680,035 B2 | 3/2014 | Kuhlman et al. |
| 8,699,751 B2 | 4/2014 | Maladen |
| 8,709,385 B2 | 4/2014 | Tamarkin |
| 8,741,363 B2 | 6/2014 | Albrecht et al. |
| 8,771,765 B1 | 7/2014 | Fernandez |
| 8,795,635 B2 | 8/2014 | Tamarkin et al. |
| 8,883,698 B2 | 11/2014 | Scheibel et al. |
| 9,006,162 B1 | 4/2015 | Rizk |
| 9,186,642 B2 | 11/2015 | Dihora et al. |
| 9,265,727 B1 | 2/2016 | Lowenborg |
| 9,296,550 B2 | 3/2016 | Smith |
| 9,308,398 B2 | 4/2016 | Hutton et al. |
| 9,428,616 B2 | 8/2016 | Wagner |
| 9,512,275 B2 | 12/2016 | Wagner |
| 9,610,239 B2 | 4/2017 | Feng |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,311,575 B2 | 6/2019 | Stofel |
| 10,426,713 B2 | 10/2019 | Song |
| 10,441,519 B2 | 10/2019 | Zhao |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1* | 5/2003 | Goldberg ............ C11D 3/0094 510/130 |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180246 A1 | 9/2003 | Frantz et al. |
| 2003/0185867 A1 | 10/2003 | Kerschner et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0144863 A1 | 7/2004 | Kendrick |
| 2004/0229963 A1 | 11/2004 | Stephane |
| 2004/0234484 A1 | 11/2004 | Peffly |

(56) References Cited

U.S. PATENT DOCUMENTS

| | | |
|---|---|---|
| 2004/0235689 A1 | 11/2004 | Sakai et al. |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0201967 A1 | 9/2005 | Albrecht et al. |
| 2005/0202984 A1 | 9/2005 | Schwartz et al. |
| 2005/0233929 A1 | 10/2005 | Queen |
| 2006/0002880 A1 | 1/2006 | Peffly |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0090777 A1 | 5/2006 | Hecht et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0183662 A1 | 8/2006 | Crotty et al. |
| 2006/0210139 A1 | 9/2006 | Carroll |
| 2006/0229227 A1 | 10/2006 | Goldman |
| 2006/0252662 A1 | 11/2006 | Soffin |
| 2006/0276357 A1 | 12/2006 | Smith, III et al. |
| 2006/0292104 A1 | 12/2006 | Guskey |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0292380 A1 | 12/2007 | Staudigel |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0206179 A1 | 8/2008 | Peffly et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0246236 A1 | 10/2009 | Kitko |
| 2009/0312224 A1 | 12/2009 | Yang et al. |
| 2009/0324505 A1 | 12/2009 | Seidling |
| 2010/0183539 A1 | 7/2010 | Bernhardt |
| 2010/0310644 A1 | 12/2010 | Liebmann |
| 2011/0008267 A1 | 1/2011 | Arkin et al. |
| 2011/0165107 A1 | 7/2011 | Derks et al. |
| 2011/0171155 A1 | 7/2011 | Federle |
| 2011/0232668 A1 | 9/2011 | Hoffmann et al. |
| 2011/0245126 A1 | 10/2011 | Tsaur et al. |
| 2011/0268778 A1 | 11/2011 | Dihora |
| 2011/0269657 A1 | 11/2011 | Dihora et al. |
| 2011/0305739 A1 | 12/2011 | Royce |
| 2011/0319790 A1 | 12/2011 | Kost et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0100091 A1 | 4/2012 | Hata et al. |
| 2012/0100092 A1 | 4/2012 | Murray |
| 2012/0291911 A1 | 11/2012 | Smith |
| 2012/0309660 A1 | 12/2012 | Kawasoe |
| 2012/0316095 A1 | 12/2012 | Wei et al. |
| 2013/0034515 A1 | 2/2013 | Stone et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0147025 A1 | 5/2014 | Periaswamy |
| 2014/0162979 A1 | 6/2014 | Palla-venkata |
| 2014/0171471 A1 | 6/2014 | Krueger |
| 2014/0216495 A1 | 8/2014 | Bureiko |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0110728 A1 | 4/2015 | Jayaswal |
| 2015/0147286 A1 | 5/2015 | Barrera |
| 2015/0218496 A1 | 8/2015 | Schmiedel et al. |
| 2015/0262354 A1 | 9/2015 | Periaswamy |
| 2015/0297489 A1 | 10/2015 | Kleinen |
| 2015/0299400 A1 | 10/2015 | Wagner et al. |
| 2015/0313818 A1 | 11/2015 | Stagg |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0235643 A1 | 8/2016 | Mathonneau et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |

(56) References Cited

U.S. PATENT DOCUMENTS

| | | |
|---|---|---|
| 2016/0317424 A1 | 11/2016 | Kadir |
| 2016/0354300 A1 | 12/2016 | Thompson et al. |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0239155 A1 | 8/2017 | Hartnett |
| 2017/0252273 A1 | 9/2017 | Renock et al. |
| 2017/0278249 A1 | 9/2017 | Stofel et al. |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2018/0044097 A1 | 2/2018 | Zeik |
| 2018/0057451 A1 | 3/2018 | Owens et al. |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0221266 A1 | 8/2018 | Zhao et al. |
| 2018/0256481 A1 | 9/2018 | Glenn, Jr. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2019/0105242 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0142711 A1 | 5/2019 | Torres Rivera |
| 2019/0167554 A1 | 6/2019 | Wankhade |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0365633 A1 | 12/2019 | Glenn, Jr. |
| 2020/0000690 A1 | 1/2020 | Renock |
| 2020/0129402 A1 | 4/2020 | Jamadagni |
| 2020/0163846 A1 | 5/2020 | Song |
| 2021/0022986 A1 | 1/2021 | Glenn, Jr. |

FOREIGN PATENT DOCUMENTS

| | | |
|---|---|---|
| CN | 102697668 B | 8/2013 |
| CN | 103356408 A | 10/2013 |
| CN | 102697670 B | 7/2014 |
| CN | 102851015 B | 12/2014 |
| CN | 105726393 A | 7/2016 |
| CN | 105769617 A | 7/2016 |
| CN | 106750361 A | 5/2017 |
| DE | 4315396 A1 | 11/1994 |
| DE | 202005009618 U1 | 9/2005 |
| DE | 102015204987 A1 | 9/2016 |
| EP | 0574086 A2 | 12/1993 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 2042216 B1 | 9/2015 |
| JP | S56011009 A | 12/1981 |
| JP | 58113300 | 7/1983 |
| JP | S58113300 A | 7/1983 |
| JP | S61236708 A | 10/1986 |
| JP | H04364114 A | 12/1992 |
| JP | 07252134 A | 10/1995 |
| JP | H08310924 A | 11/1996 |
| JP | 09020618 A | 1/1997 |
| JP | 09030938 A | 2/1997 |
| JP | H09175961 A | 7/1997 |
| JP | 2964226 B2 | 10/1999 |
| JP | 3069802 B2 | 7/2000 |
| JP | 2003201217 A | 12/2001 |
| JP | 2002179552 A | 6/2002 |
| JP | 2002226889 A | 8/2002 |
| JP | 2003055699 A | 2/2003 |
| JP | 3480165 B2 | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006124312 A | 5/2006 |
| JP | 2006183039 A | 7/2006 |
| JP | 2006193549 A | 7/2006 |
| JP | 2007131687 A | 5/2007 |
| JP | 2008001626 A | 1/2008 |
| JP | 2008214292 A | 9/2008 |
| JP | 2009096778 A | 5/2009 |
| JP | 2011153167 A | 8/2011 |
| JP | 2011190221 A | 9/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 6046394 B2 | 1/2014 |
| JP | 2014024875 A | 2/2014 |
| JP | 2014091723 A | 5/2014 |
| JP | 5667790 B2 | 2/2015 |
| JP | 2015101545 A | 6/2015 |
| JP | 2018012673 A | 1/2018 |
| KR | 1020080111280 | 12/2008 |
| KR | 20140060882 A | 5/2014 |
| WO | 9114759 A1 | 10/1991 |
| WO | 91017237 A1 | 11/1991 |
| WO | 9213520 A1 | 8/1992 |
| WO | WO199325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | 9924013 A1 | 5/1999 |
| WO | WO9924004 A1 | 5/1999 |
| WO | 9949837 A1 | 10/1999 |
| WO | WO0012553 A1 | 3/2000 |
| WO | WO0142409 A1 | 6/2001 |
| WO | WO0148021 A1 | 7/2001 |
| WO | 2004078901 A1 | 9/2004 |
| WO | WO2005023975 A1 | 3/2005 |
| WO | 2008145582 A1 | 12/2008 |
| WO | WO2009016555 A1 | 2/2009 |
| WO | WO2009053931 A2 | 4/2009 |
| WO | WO2010052147 A2 | 5/2010 |
| WO | 2012017091 A2 | 2/2012 |
| WO | WO2012055587 A1 | 5/2012 |
| WO | WO2012084970 A1 | 6/2012 |
| WO | WO2013010706 A1 | 1/2013 |
| WO | 2014073245 A1 | 5/2014 |
| WO | WO2014148245 A1 | 9/2014 |
| WO | 2015122371 A1 | 8/2015 |

(56) References Cited

FOREIGN PATENT DOCUMENTS

| WO | WO2016147196 A1 | 9/2016 |
|---|---|---|
| WO | 2017052161 A1 | 3/2017 |
| WO | WO2017140798 A1 | 8/2017 |
| WO | WO2017207685 A1 | 12/2017 |
| WO | WO2018023180 A1 | 2/2018 |

OTHER PUBLICATIONS

U.S. Appl. No. 16/170,711, filed Oct. 25, 2018, Jamadagni et al.
U.S. Appl. No. 16/248,900, filed Jan. 16, 2019, Torres Rivera et al.
U.S. Appl. No. 16/285,535, filed Feb. 26, 2019, Zhao et al.
U.S. Appl. No. 16/226,927, filed Dec. 20, 2018, Glenn, Jr. et al.
U.S. Appl. No. 16/226,914, filed Dec. 20, 2018, Gillis et al.
U.S. Appl. No. 16/376,033, filed Apr. 5, 2019, Zhao et al.
U.S. Appl. No. 16/390,270, filed Apr. 22, 2019, Torres Rivera et al.
"Natural Detangling Shampoo", Mintel Database, Sep. 13, 2017.
"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 16/156,045.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.
All Final and Non-Final Office Actions for U.S. Appl. No. 15/135,701.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.
All Final and Non-Final Office Actions for U.S. Appl. No. 15/299,860.
All final and non-final office actions for U.S. Appl. No. 15/379,660.
All final and non-final office actions for U.S. Appl. No. 15/379,674.
All final and non-final office actions for U.S. Appl. No. 15/448,911.
All final and non-final office actions for U.S. Appl. No. 15/467,317.
All Final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.
All Final and Non-Final Office Actions for U.S. Appl. No. 15/789,172.
All Final and Non-Final Office Actions for U.S. Appl. No. 15/789,188.
All Final and Non-Final Office Actions for U.S. Appl. No. 15/789,208.
All Final and Non-final Office Actions for U.S. Appl. No. 15/923,499.
All final and non-final office actions for U.S. Appl. No. 15/962,327.
All final and non-final office actions for U.S. Appl. No. 15/962,351.
All final and non-final office actions for U.S. Appl. No. 16/001,045.
All final and non-final office actions for U.S. Appl. No. 16/001,053.
All final and non-final office actions for U.S. Appl. No. 16/001,058.
All final and non-final office actions for U.S. Appl. No. 16/001,064.
All Final and Non-Final Office Actions for U.S. Appl. No. 16/156,015.
All Final and Non-Final Office Actions for U.S. Appl. No. 16/156,053.
All Final and Non-Final Office Actions for U.S. Appl. No. 16/156,066.
All final and non-final office actions for U.S. Appl. No. 16/165,016.
All final and non-final office actions for U.S. Appl. No. 16/165,033.
All final and non-final office actions for U.S. Appl. No. 16/165,044.
All final and non-final office actions for U.S. Appl. No. 16/170,498.
All final and non-final office actions for U.S. Appl. No. 16/170,516.
All final and non-final office actions for U.S. Appl. No. 16/170,711.
All final and non-final office actions for U.S. Appl. No. 16/226,914.
All final and non-final office actions for U.S. Appl. No. 16/226,927.
All final and non-final office actions for U.S. Appl. No. 16/248,900.
All final and non-final office actions for U.S. Appl. No. 16/285,535.
All final and non-final office actions for U.S. Appl. No. 16/376,033.
All final and non-final office actions for U.S. Appl. No. 16/390,270.

Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018.
Carbopol Aqua SF-1 Polymer Technical Data Sheet, TDS-294, Dec. 2000.
Christensen et al., "Experimental Determination of Bubble Size Distribution in a Water Column by Interferometric Particle Imaging and Telecentric Direct Image Method", Student Report, Aalborg University, Jun. 3, 2014.
Dehyquart Guar: Published Nov. 2010.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018, p. 1.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 19, 2017.
PCT International Search Report and Written Opinion for PCT/US2017/057497 dated Jan. 9, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.
PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.
PCT International Search Report and Written Opinion for PCT/US2018/036185 dated Aug. 3, 2018.
PCT International Search Report and Written Opinion for PCT/US2018/055102 dated Jan. 9, 2019.

(56) References Cited

OTHER PUBLICATIONS

PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/056673 dated Feb. 5, 2019.
PCT International Search Report and Written Opinion for PCT/US2018/056674 dated Feb. 5, 2019.
PCT International Search Report and Written Opinion for PCT/US2018/057451 dated Feb. 25, 2019.
PCT International Search Report and Written Opinion for PCT/US2018/057476 dated Jan. 18, 2019.
PCT International Search Report and Written Opinion for PCT/US2018/066697 dated Mar. 15, 2019.
PCT International Search Report and Written Opinion for PCT/US2018/066701 dated Mar. 15, 2019.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018.
Practical Modem Hair Science, Published 2012.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.
"Deep Image Matting", Ning Xu et al, Beckman Institute for Advanced Science and Technology, University of Illinois at Urbana-Champaign, Adobe Research, Mar. 10, 2017.
U.S. Appl. No. 16/532,556, filed Aug. 7, 2019, Song et al.
All final and non-final office actions for U.S. Appl. No. 16/532,556.
PCT International Search Report and Written Opinion for PCT/US2019/025923 dated Jun. 24, 2019.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012.
All final and non-final office actions for U.S. Appl. No. 16/846,594.
Musazzi, "Emulsion versus nonoemulsion: how much is the formulative shift critical for a cosmetic product?" (Drug Deliv. and Trans. Res. (2018) 8:414-421 (Year: 2018).
PCT International Search Report and Written Opinion for PCT/US2019/057974 dated Feb. 3, 2020.
U.S. Appl. No. 16/846,594, filed Apr. 13, 2020, Torres Rivera et al.
D'Souza et al., Shampoo and Conditioners: What a Dermatologist Should Know? Indian J Dermatol, May-Jun. 2015 60(3), 248-254 (2015).
Inspection cerlilicate for Hostapon® CCG, Clariant Iberica Production, S.A., May 6, 2019.
Product Bulletin, Amphosol® CG, Cocamidopropyl Betaine, Stepan Company, Jun. 2011.
Product Data Sheet for Chemoryl™ LS Surfactant, Sodium Lauroyl Sarcosinate, Lubrizol Advanced Materials, Inc., Mar. 24, 2020.
Product Data Sheet, Eversoft™ UCS-40S, Disodium Cocoyl Glutamate (Sodium Cocoyl Glutamate*), Sino Lion USA, Jul. 2018.
Product Fact Sheet—Hostapon® CCG, mild anionic surfactant for the cosmetic industry, Clariant International Ltd., Aug. 2014.
Product Fact Sheet, Hostapon® CGN, Mild anionic surfactant for the cosmetic industry, Clariant International Ltd., Jan. 2016.
UL Prospector® Product Data Sheet, Plantacare® 818 UP, C8-16 fatty alcohol glucoside, BASF, May 21, 2015.
All final and non-final office actions for U.S. Appl. No. 17/071,033.
Fevola, Michael J. "Guar Hydroxypropyltrimonium Chloride." Cosmetics and toiletries 127.1 (2012) 16-21.
Medvedev, Diffusion Coefficients in Multicomponent Mixtures, PhD Thesis from Technical University of Denmark, 2005, 181 pages.
PERM Inc,, Diffusion Coefficient: Measurement Techiques, https://perminc.com/resources/fundamentals-of-fluid-flow-in-porous-media/chapter-3-molecular-diffusion/diffusion-coefficient/measurement-techniques, Oct. 2020.
Robinson et al., Final Report of the Amended Safety Assessment of Sodium Laureth Sulfate and Related Salts of SulfatedEthoxylated Alcohols, International Journal of Toxicology 29(Supplement 3) 151S-161S, 2010 (Year: 2010).
U.S. Appl. No. 17/071,033, filed Oct. 15, 2020, Glenn, Jr. et al.
All Final and Non-Final Office Actions for U.S. Appl. No. 15/135,696.
All Final and Non-Final Office Actions for U.S. Appl. No. 15/788,938.
All Final and Non-Final Office Actions for U.S. Appl. No. 15/788,957.
"Anti-Dandruff Shampoo", Mintel Database, Record No. 752198, dated Aug. 2007 ; pp. 1-3.
"Dandruff Control Shampoo", Mintel Database, Record No. 2300131, dated Jan. 2014; pp. 1-2.
Parchem fine & specialty chemicals. MIPA-laureth sulfate supplier distributor-CAS 83016-76-6; dated 2021; pp. 1-7.

* cited by examiner

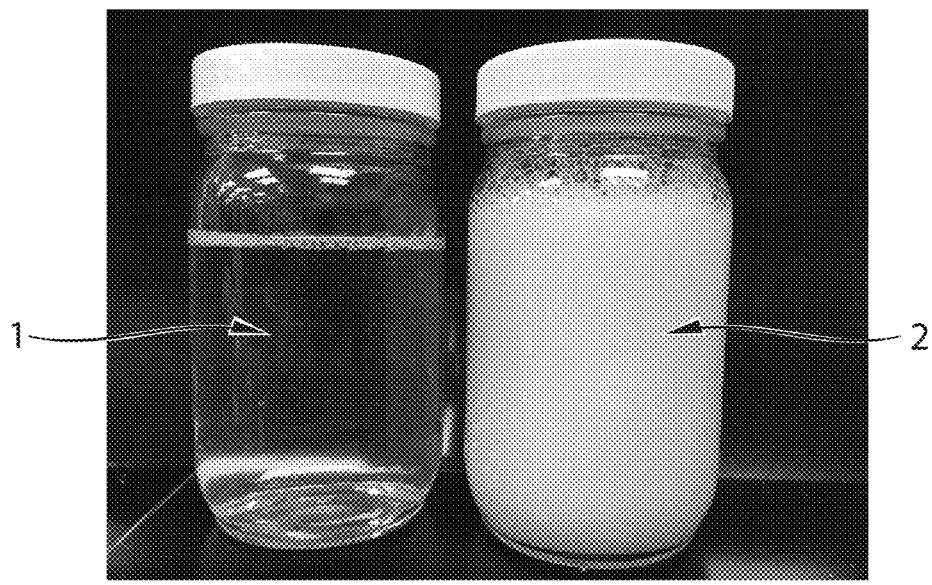

COMPACT SHAMPOO COMPOSITION CONTAINING SULFATE-FREE SURFACTANTS

FIELD OF THE INVENTION

The present invention relates to compact shampoo compositions. More particularly a clear, stable, compact shampoo composition that is substantially free of sulfate-based surfactants and contains sodium cocoyl isethionate.

BACKGROUND OF THE INVENTION

Some consumers desire a shampoo composition in a foam form. Given the low density of the foam, shampoo ingredients may be present at a higher concentration. For instance, compact shampoo compositions can contain a high concentration of surfactant, to deliver enough surfactant for proper cleaning and lather during use.

Furthermore, shampoos typically employ sulfate-based surfactant systems because of their effectiveness in generating high lather volume and good lather stability and cleaning. However, some consumers believe that sulfate-based surfactants, like sodium lauryl sulfate and sodium laureth sulfate, can be less gentle to the hair and skin, especially colored hair, as compared to shampoos that are substantially free of sulfate-based surfactant systems.

Therefore, some consumers may prefer a shampoo composition that is substantially free of sulfate-based surfactants. However, it can be difficult to use these surfactants in traditional liquid shampoos because it is difficult to formulate a composition that has acceptable lather volume, cleansing, stability, and clarity. To improve lather volume and cleansing, shampoos containing sulfate-free surfactants may contain fatty acyl isethionates. However, fatty acyl isethionate has a low solubility in water (typically 0.01% by weight at 25° C.), which is an obstacle to incorporating it into aqueous compositions. Therefore, fatty acyl isethionates, like sodium cocyl isethionate, are generally used at relatively low levels because the low solubility can lead to crystallization if incorporated at higher levels. Even when a shampoo contains a low level of sodium cocyl isethionate (i.e. 2%-5%, a level where there is no crystallization at ambient temperature), the shampoo can turn cloudy at low temperatures (e.g. ≤5° C.) due to the high Krafft point of sodium cocyl isethionate.

The problems with formulating with sodium cocyl isethionate can be exacerbated when making a compact shampoo. For instance, compact shampoo compositions may require a higher level of sodium cocyl isethionate (e.g. from about 3% to about 8%) to obtain the cleaning and lather benefits and therefore it can be difficult to have a shampoo product that is stable and clear without crystallization at both ambient temperature and low temperatures (e.g. ≤5° C.).

Therefore, there is a need for a clear, stable, compact shampoo composition that is substantially free of sulfate-based surfactants and contains sodium cocoyl isethionate.

SUMMARY OF THE INVENTION

A compact shampoo composition comprising: (a) from about 20% to about 40%, by weight of the composition, of a surfactant system wherein the surfactant system comprises: (i) from about 5% to about 20%, by weight of the composition, acyl glutamate; (ii) from about 2% to about 8% sodium cocoyl isethionate; (iii) from about 5% to about 12% zwitterionic surfactant; wherein the ratio of zwitterionic surfactant to sodium cocol isethionate is greater than 1.5; wherein the composition is clear and stable after storage at ambient temperature and at 5° C.; and wherein the shampoo composition is substantially free of sulfate-based surfactants.

A compact shampoo composition comprising: (a) from about 20% to about 35%, by weight of the composition, of a surfactant system wherein the surfactant system comprises: (i) from about 10% to about 20%, by weight of the composition, acyl glutamate; (ii) from about 2% to about 6% sodium cocoyl isethionate; (iii) from about 7% to about 10% zwitterionic surfactant; wherein the ratio of zwitterionic surfactant to sodium cocol isethionate is from about 1.5 to about 2.5; wherein the composition is clear and stable after storage at ambient temperature and at 5° C.; and wherein the shampoo composition is substantially free of sulfate-based surfactants.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIGURE is a digital photograph of two example shampoo compositions where one composition is clear and one composition is cloudy.

DETAILED DESCRIPTION OF THE INVENTION

While the specification concludes with claims particularly pointing out and distinctly claiming the invention, it is believed that the present disclosure will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of."

As used herein, the term "fluid" includes liquids, gels, emulsions, or suspensions.

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC").

As used herein, "personal care composition" includes hair care products such as shampoos, conditioners, conditioning shampoos, hair colorants, as well as shower gels, liquid hand cleansers, facial cleansers, laundry detergent, dish detergent, and other surfactant-based liquid compositions.

As used herein, "substantially free" means less than 3%, alternatively less than 2%, alternatively less than 1%, alternatively less than 0.5%, alternatively less than 0.25%, alternatively less than 0.1%, alternatively less than 0.05%, alternatively less than 0.01%, alternatively less than 0.001%, and/or alternatively free of. As used herein, "free of" means 0%.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the shampoo composition.

Shampoo Composition

As will be described herein, stable, compact shampoo compositions are disclosed that are substantially free of sulfate-based surfactants and contain sodium cocoyl isethionate. The compact shampoo can have a low liquid phase viscosity so it can be delivered through an aerosol and/or mechanical pump foamer.

It can be difficult to make shampoo compositions that are substantially free of sulfate-based surfactants because it can be difficult to formulate a composition that has acceptable lather volume, cleansing, stability, and clarity. These problems can be exacerbated when making a compact formula, which has a higher surfactant level and it can be even more complex when the compact shampoo contains sodium cocyl isethionate. One significant problem in formulating these compositions is making it stable and clear without crystallization at ambient (20-25° C.) and low (≤5° C.) temperatures.

Examples A-D, discussed hereafter, could be preferred by consumers over Comparative Examples 1-9 because they are stable at ambient temperature and at 5° C. Examples A-D contain from 25% to 30% total surfactant, which includes 15% disodium cocoyl glutamate, 3% to 5% sodium cocoyl isethionate, and 7% to 10% zwitterionic surfactant. It was unexpectedly found that using more than about 5% zwitterionic surfactant, like LAPB or CAPB, the product does not turn cloudy when exposed to low temperature, therefore making a consumer acceptable clear and phase stable shampoo product.

The shampoo compositions can have a viscosity from about 1 cP to about 5000 cP, from about 2 cP to about 3000 cP, from about 5 cP to about 2000 cP, from about 10 cP to about 1000 cP, from about 10 cP to about 500 cP, and/or from about 20 cP to about 100 cP. The shampoo compositions can have a viscosity less than 100 cP, less than 80 cP, less than 60 cP, less than 50 cP, less than 40 cP, less than 30 cP, and/or less than 25 cP, at constant shear rate of 2000 $s^{-1}$ and at temperature of 26.5° C., as determined by the Cone/Plate Viscosity Measurement, described hereafter.

The shampoo compositions can be phase stable and can be substantially free of a viscosity reducing agent or hydrotrope. Non-limiting examples of viscosity reducing agents can include propylene glycol, dipropylene glycol, alcohols, glycerin, and combinations thereof.

The shampoo compositions can be phase stable and can be substantially free of a thickener. Non-limiting examples of thickeners can include polyacrylate polymers such as Carbopol® SF-1 and other Carbopol® thickeners, gum thickeners such as xanthan gum, and combinations thereof.

The shampoo compositions can have a pH from about 2 to about 10, from about 4 to about 8, from about from about 5 to about 7, and/or about 6.

The neat shampoo composition can appear clear and/or translucent. The neat shampoo composition can have a percent transmittance (% T) of at least 75%, alternatively at least 80%, alternatively at least 85%, and alternatively at least 90%, as measured by the Light Transmittance Method described hereafter.

Surfactant

The shampoo compositions described herein can include one or more surfactants in the surfactant system and the one or more surfactants can be substantially free of sulfate-based surfactants. As can be appreciated, surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a shampoo composition can include anionic moieties to allow for the formation of a coacervate with a cationic polymer. The surfactant can be selected from anionic surfactants, amphoteric surfactants, zwitterionic surfactants, non-ionic surfactants, and combinations thereof.

Shampoo compositions typically employ sulfate-based surfactant systems (such as, but not limited to, sodium lauryl sulfate) because of their effectiveness in lather production, stability, clarity and cleansing. The foamed shampoo compositions described herein can be substantially free of sulfate-based surfactants.

The concentration of the surfactant in the composition should be sufficient to provide the desired cleaning and lather performance. The shampoo composition can comprise a total surfactant level of from about 10% to about 50%, by weight, from about 15% to about 48%, by weight, from about 18% to about 45%, by weight, from about 20% to about 40%, by weight, from about 22% to about 38%, from about 23% to about 35%, and/or from about 25% to about 30%.

Suitable surfactants that are substantially free of sulfates can include isethionates, sulfonates, sulfosuccinates, sulfoacetates, acyl glucosides, acyl glycinates, acyl sarcosinare, acyl glutamates, acyl alaninates, glucamide, glucose carboxylates, amphoacetates, taurates, other acyl aminoacids, betaines, sultaines, and/or phosphate esters. Suitable surfactants that are substantially free of sulfates can contain carboxylic acids.

The foamed shampoo composition can contain an anionic surfactant. The composition can comprise a total anionic surfactant level from about 5% to about 40%, by weight, from about 8% to about 35%, by weight, from about 10% to about 35%, by weight, from about 10% to about 30%, by weight, from about 13% to about 25%, by weight, from about 15% to about 23%, by weight, from about 15% to about 22%, from about 17% to about 21%, and/or from about 18% to about 20%.

The surfactant system can contain from about 50% to about 85% anionic surfactant, by weight of the surfactant system, from about 55% to about 80% anionic surfactant, by weight of the surfactant system, from about 60% to about 78%, and/or from about 65% to about 76%, and/or from about 66% to about 73%.

The composition can contain a primary surfactant that can be an anionic surfactant and the anionic surfactant can be a glutamate, for instance an acyl glutamate. The composition can comprise an acyl glutamate level from about 2% to about 25%, by weight, from about 5% to about 20%, by weight, 10% to about 18%, by weight, and/or from about 12% to about 15%, by weight. The composition can contain less than 20%, by weight, acyl glutamate, less than 18%, less than 16%, and/or less than 15%.

The ratio of acyl glutamate to total surfactant can be less than 0.6, less than 0.58, less than 0.55, less than 0.53, and/or less than or equal to 0.51. The ratio of acyl glutamate to total surfactant can be from about 0.05 to about 0.6, from about 0.1 to about 0.58, from about 0.15 to about 0.55, from about 0.20 to about 0.53, and/or from about 0.25 to about 0.05.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl Glutamate, sodium olivoyl glutamate, disodium olivoyl glutamate, sodium palmoyl glutamate, disodium palmoyl Glutamate, TEA-cocoyl glutamate, TEA-hydrogenated tallowoyl glutamate, TEA-lauroyl glutamate, and mixtures thereof.

The composition can contain one or more co-surfactants selected from the group consisting of an anionic co-surfactant, zwitterionic surfactant, non-ionic surfactant, and combinations thereof. The composition can contain a primary surfactant that can be an acyl glutamate and the co-surfactant can be an isethionate or a sulfosuccinate.

The anionic co-surfactant can be selected from the group consisting of isethionates, sarcosinates, sulfosuccinates, sulfonates, sulfoacetates, acyl glycinates, acyl alaninates, glucose carboxylates, alkyl ether carboxylates, alkyl amphoacetates, acyl taurates, and mixture thereof. The composition can comprise an anionic co-surfactant level can be from about 0% to about 10%, by weight, from about 1% to about 8%, by weight, from about 2% to about 7%, by weight, from about 1% to about 6%, by weight, and/or from about 3% to about 5%.

The weight ratio of primary surfactant to anionic co-surfactant can be from about 1:1 to about 10:1, from about 3:2 to about 7:1, and/or from about 3:1 to about 5:1. The weight ratio of primary surfactant to anionic co-surfactant can be less than 5:1.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lahroyl-glutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palinitoyl sarcosinate, TEA-cocoyl sarcosinate, TEA-lauroyl sarcosinate, TEA-oleoyl sarcosinate, TEA-palm kernel sarcosinate, and combinations thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfonates can include alpha olefin sulfonates, linear alkylbenzene sulfonates, sodium laurylglucosides hydroxypropylsulfonate and combination thereof.

Non-limiting examples of sulfoacetates can include sodium lauryl sulfoacetate, ammonium lauryl sulfoacetate and combination thereof.

Non-limiting example of acyl glycinates can include sodium cocoyl glycinate, sodium lauroyl glycinate and combination thereof.

Non-limiting example of acyl alaninates can include sodium cocoyl alaninate, sodium lauroyl alaninate, sodium N-dodecanoyl-1-alaninate and combination thereof.

Non-limiting example of glucose carboxylates can include sodium lauryl glucoside carboxylate, sodium cocoyl glucoside carboxylate and combinations thereof.

Non-limiting example of alkyl ether carboxylate can include sodium laureth-4 carboxylate, laureth-5 carboxylate, laureth-13 carboxylate, sodium C12-13 pareth-8 carboxylate, sodium C12-15 pareth-8 carboxylate and combination thereof.

Non-limiting example of alkylamphoacetates can include sodium cocoyl amphoacetate, sodium lauroyl amphoacetate and combination thereof.

Non-limiting example of acyl taurates can include sodium methyl cocoyl taurate, sodium methyl lauroyl taurate, sodium methyl oleoyl taurate and combination thereof.

The surfactant system may further comprise one or more zwitterionic surfactants and the zwitterionic surfactant can be a co-surfactant selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

Examples of betaine zwitterionic surfactants can include coco dimethyl carboxymethyl betaine, cocoamidopropyl betaine (CAPB), cocobetaine, lauryl amidopropyl betaine (LAPB), oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

The zwitterionic surfactant can comprise cocamidopropyl betaine (CAPB), lauramidopropyl betaine (LAPB), and combinations thereof.

The foamed shampoo composition can comprise a zwitterionic surfactant level from about 1% to about 20%, by weight, from about 5% to about 15%, by weight, from about 6% to about 12%, by weight, and/or from about 7% to about 12%, by weight. The surfactant system can contain from about 15% to about 40% zwitterionic surfactant, by weight of the surfactant system, from about 22% to about 37%, from about 25% to about 35%.

The surfactant system can have a weight ratio of anionic surfactant to zwitterionic surfactant from about 1:2 to about 5:1, from about 1:1 to about 7:2, from about 3:2 to about 3:1, and/or from about 2:1 to about 5:2. The surfactant system can have a weight ratio of anionic surfactant to zwitterionic surfactant less than 4:1, less than 3:1, and/or less than or equal to 5:2.

The surfactant system can have a weight ratio of zwitterionic surfactant to anionic co-surfactant of from about 1:1 to about 5:1, from about 5:4 to about 4:1, from about 3:2 to about 3:1, and/or from about 3:2 to about 5:2. The surfactant system can have a weight ratio zwitterionic surfactant to anionic co-surfactant greater than 1:1, greater than 5:4, and/or greater than 3:2.

The surfactant system can have a weight ratio of zwitterionic surfactant to sodium cocoyl isethionate of from about 1:1 to about 5:1, from about 5:4 to about 4:1, from about 3:2 to about 3:1, and/or from about 3:2 to about 5:2. The surfactant system can have a weight ratio zwitterionic surfactant to sodium cocoyl isethionate greater than 1:1, greater than 5:4, and/or greater than 3:2.

The foamed shampoo composition can comprise a non-ionic surfactant select from alkyl glucoside, acyl glucamide and other non-ionic surfactants. Non-limiting examples of alkyl glucosides can include decyl glucoside, cocoyl glucoside, lauroyl glucoside and combination thereof.

Non-limiting examples of acyl glucamide can include lauroyl/myristoyl methyl glucamide, capryloyl/caproyl methyl glucamide, lauroyl/myristoyl methyl glucamide, cocoyl methyl glucamide and combinations thereof.

Liquid Carrier

Inclusion of an appropriate quantity of a liquid carrier can facilitate the formation of a shampoo composition having an appropriate liquid viscosity and rheology. A shampoo composition can include, by weight of the composition, about 50% to about 95%, of a liquid carrier, about 60% to about 85%, about 65% to about 80%, about 68% to about 78%, and/or about 70% to about 77%.

A liquid carrier can be water, or can be a miscible mixture of water and organic solvent. A liquid carrier can be water with minimal or no significant concentrations of organic solvent, except as otherwise incidentally incorporated into the composition as minor ingredients of other essential or optional components. Suitable organic solvents can include water solutions of lower alkyl alcohols and polyhydric alcohols. Useful lower alkyl alcohols include monohydric alcohols having 1 to 6 carbons, such as ethanol and isopropanol. Exemplary polyhydric alcohols include propylene glycol, hexylene glycol, glycerin, and propane diol.

Optional Ingredients

As can be appreciated, shampoo compositions described herein can include a variety of optional components to tailor the properties and characteristics of the composition. As can be appreciated, suitable optional components are well known and can generally include any components which are physically and chemically compatible with the essential components of the shampoo compositions described herein. Optional components should not otherwise unduly impair product stability, aesthetics, or performance. Individual concentrations of optional components can generally range from about 0.001% to about 10%, by weight of a shampoo composition. Optional components can be further limited to components which will not impair the clarity of a translucent shampoo composition.

Optional components may include, but are not limited to, conditioning agents (including hydrocarbon oils, fatty esters, silicones), cationic polymers, anti-dandruff actives, chelating agents, and natural oils such as sun flower oil or castor oil. Additional suitable optional ingredients include but are not limited to perfumes, perfume microcapsules, colorants, particles, anti-microbials, foam boosters, anti-static agents, propellants, self-foaming agents, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Silicone Conditioning Agent

A shampoo composition can include a silicone conditioning agent. Suitable silicone conditioning agents can include volatile silicone, non-volatile silicone, or combinations thereof. A silicone conditioning agent, the agent can be included from about 0.01% to about 10% active silicone material, by weight of the composition, from about 0.1% to about 8%, from about 0.1% to about 5%, and/or from about 0.2% to about 3%. Examples of suitable silicone conditioning agents, and optional suspending agents for the silicone, are described in U.S. Reissue Pat. No. 34,584, U.S. Pat. No. 5,104,646, and U.S. Pat. No. 5,106,609, each of which is incorporated by reference herein. Suitable silicone conditioning agents can have a viscosity, as measured at 25° C., from about 20 centistokes ("csk") to about 2,000,000 csk, from about 1,000 csk to about 1,800,000 csk, from about 50,000 csk to about 1,500,000 csk, and from about 100,000 csk to about 1,500,000 csk.

The dispersed silicone conditioning agent particles can have a volume average particle diameter ranging from about 0.01 micrometer to about 50 micrometer. For small particle application to hair, the volume average particle diameters can range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), which is incorporated herein by reference.

Silicone emulsions suitable for the shampoo compositions described herein can include emulsions of insoluble polysiloxanes prepared in accordance with the descriptions provided in U.S. Pat. No. 4,476,282 and U.S. Patent Application Publication No. 2007/0276087 each of which is incorporated herein by reference. Suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion can further include an additional emulsifier together with the anionic surfactant.

Other classes of silicones suitable for the shampoo compositions described herein can include i) silicone fluids, including silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The silicone conditioning agent can be a silicone emulsion having particles size less than about 10 microns, less than 1 microns and less than 0.1 microns.

Organic Conditioning Materials

The conditioning agent of the shampoo compositions described herein can also include at least one organic conditioning material such as oil or wax, either alone or in combination with other conditioning agents, such as the silicones described above. The organic material can be non-polymeric, oligomeric or polymeric. The organic material can be in the form of an oil or wax and can be added in the personal care formulation neat or in a pre-emulsified form. Suitable examples of organic conditioning materials can include: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Cationic Polymer

A shampoo composition can include a cationic polymer to allow formation of a coacervate, particularly formation of a coacervate during use. As can be appreciated, the cationic charge of a cationic polymer can interact with an anionic charge of a surfactant to form the coacervate. Suitable cationic polymers can include: a cationic guar polymer, a cationic non-guar galactomannan polymer, a cationic starch polymer, a cationic copolymer of acrylamide monomers and cationic monomers, a synthetic, non-crosslinked, cationic polymer, which may or may not form lyotropic liquid crystals upon combination with the detersive surfactant, and a cationic cellulose polymer.

A cationic polymer can be included by weight of the shampoo composition at about 0.01% to about 2%, about 0.05% to about 1%, about 0.1% to about 0.8%, and/or from about 0.1% to about 0.5%. Cationic polymers can have cationic charge densities of about 0.9 meq/g or more, about 1.2 meq/g or more, and about 1.5 meq/g or more. However, cationic charge density can also be about 7 meq/g or less and/or about 5 meq/g or less. The charge densities can be measured at the pH of intended use of the shampoo composition. (e.g., at about pH 3 to about pH 9; or about pH 4 to about pH 8). The average molecular weight of cationic polymers can generally be between about 1,000 and 2 million, between about 5,000 and about 1 million, and between about 10,000 and about 0.5 million. Low molecular weight cationic polymers can be preferred. Low molecular weight cationic polymers can have greater translucency in the liquid carrier of a shampoo composition. Suitable cationic polymers can include Polyquaternium-6 with a charge density of about 6.2 meq/g and a M.Wt. of about 223,000 g/mole available from Clariant, Polyquaternium-76 with a charge density of about 1.6 meq/g and a M.Wt. of about 1.1 million g/mole.

Cationic Guar Polymer

The cationic polymer can be a cationic guar polymer, which is a cationically substituted galactomannan (guar) gum derivative. Suitable guar gums for guar gum derivatives can be obtained as a naturally occurring material from the seeds of the guar plant. As can be appreciated, the guar molecule is a straight chain mannan which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums can be obtained through reactions between the hydroxyl groups of the polygalactomannan and reactive quaternary ammonium compounds. The degree of substitution of the cationic groups onto the guar structure can be sufficient to provide the requisite cationic charge density described above.

A cationic guar polymer can have a weight average molecular weight ("M.Wt.") of less than about 1 million g/mol, and can have a charge density from about 0.05 meq/g to about 2.5 meq/g. Cationic guar suitable can have a weight average molecular weight ("M.Wt.") of less than about 0.5 million g/mol.

A shampoo composition can include from about 0.01% to less than about 0.7%, by weight of the shampoo composition of a cationic guar polymer, from about 0.05% to about 0.6%, from about 0.1% to about 0.50%, by weight, and/or from about 0.1% to about 0.4%, by weight.

The cationic guar polymer can be formed from quaternary ammonium compounds which conform to general Formula II:

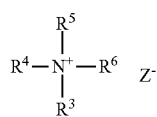

Formula II wherein where $R^3$, $R^4$ and $R^5$ are methyl or ethyl groups; and $R^6$ is either an epoxyalkyl group of the general Formula III:

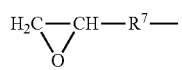

Formula III or $R^6$ is a halohydrin group of the general Formula IV:

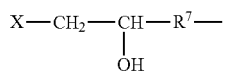

Formula IV wherein $R^7$ is a $C_1$ to $C_3$ alkylene; X is chlorine or bromine, and Z is an anion such as Cl—, Br—, I— or $HSO_4$—.

A cationic guar polymer can conform to the general formula V:

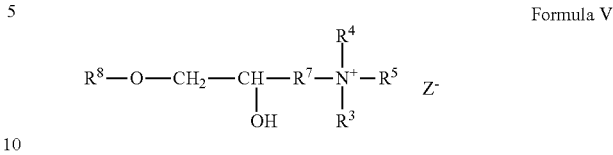

Formula V wherein $R^8$ is guar gum; and wherein $R^4$, $R^5$, $R^6$ and $R^7$ are as defined above; and wherein Z is a halogen. A cationic guar polymer can conform to Formula VI:

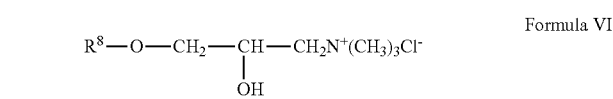

Formula VI wherein $R^8$ is guar gum.

Suitable cationic guar polymers can also include cationic guar gum derivatives, such as guar hydroxypropyltrimonium chloride. Suitable examples of guar hydroxypropyltrimonium chlorides can include the Jaguar® series commercially available from Solvay S. A., Hi-Care™ Series from Rhodia, and N-Hance™ and AquaCat™ from Ashland Inc. Jaguar® Optima has a charge density of about 1.25 meg/g and a M. Wt. of about 500,000 g/moles. Jaguar® C-500 has a charge density of 0.8 meq/g and a M.Wt. of 500,000 g/mole; Hi-Care™ 1000 has a charge density of about 0.7 meq/g and a M.Wt. of about 600,000 g/mole; -Hance™ 3269, N-Hance™ 3270 and N-Hance™ 3271 have a charge density of about 0.7 meq/g and a M.Wt. of about 425,000 g/mole; AquaCat™ PF618 and AquaCat™ CG518 have a charge density of about 0.9 meq/g and a M.Wt. of about 50,000 g/mole. N-Hance™ BF-13 and N-Hance™ BF-17 are borate (boron) free guar polymers. N-Hance™ BF-13 has a charge density of about 1.1 meq/g and M.W.t of about 800,000 and N-Hance™ BF-17 has a charge density of about 1.7 meq/g and M.W.t of about 800,000.

Cationic Non-Guar Galactomannan Polymer

A cationic polymer can be a galactomannan polymer derivative. A suitable galactomannan polymer can have a mannose to galactose ratio of greater than 2:1 on a monomer to monomer basis and can be a cationic galactomannan polymer derivative or an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers can be present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and can be affected by climate. Non-Guar Galactomannan polymer derivatives can have a ratio of mannose to galactose of greater than 2:1 on a monomer to monomer basis. Suitable ratios of mannose to galactose can also be greater than 3:1 or greater than 4:1. Analysis of mannose to galactose ratios is well known in the art and is typically based on the measurement of the galactose content.

The gum for use in preparing the non-guar galactomannan polymer derivatives can be obtained from naturally occurring materials such as seeds or beans from plants. Examples of various non-guar galactomannan polymers include Tara gum (3 parts mannose/1 part galactose), Locust bean or Carob (4 parts mannose/1 part galactose), and Cassia gum (5 parts mannose/1 part galactose).

A non-guar galactomannan polymer derivative can have a M. Wt. from about 1,000 g/mol to about 10,000,000 g/mol, and a M.Wt. from about 5,000 g/mol to about 3,000,000 g/mol.

The shampoo compositions described herein can include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure can be sufficient to provide the requisite cationic charge density.

A galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general Formulas II to VI, as defined above.

Cationic non-guar galactomannan polymer derivatives formed from the reagents described above can be represented by the general Formula VII:

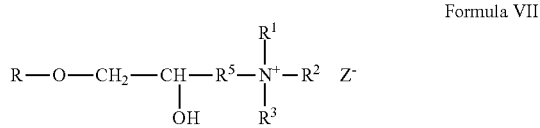

Formula VII wherein R is the gum. The cationic galactomannan derivative can be a gum hydroxypropyltrimethylammonium chloride, which can be more specifically represented by the general Formula VIII:

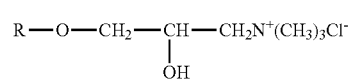

Formula VIII

The galactomannan polymer derivative can be an amphoteric galactomannan polymer derivative having a net positive charge, obtained when the cationic galactomannan polymer derivative further comprises an anionic group.

A cationic non-guar galactomannan can have a ratio of mannose to galactose which is greater than about 4:1, a M.Wt. of about 100,000 g/mol to about 500,000 g/mol, a M.Wt. of about 50,000 g/mol to about 400,000 g/mol, and a cationic charge density from about 1 meq/g to about 5 meq/g, and from about 2 meq/ g to about 4 meq/g.

Shampoo compositions can include at least about 0.05% of a galactomannan polymer derivative by weight of the composition. The shampoo compositions can include from about 0.05% to about 2%, by weight of the composition, of a galactomannan polymer derivative.

Cationic Copolymer of an Acrylamide Monomer and a Cationic Monomer

A shampoo composition can include a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

Examples of suitable cationic polymers can include:

(i) an acrylamide monomer of the following Formula IX:

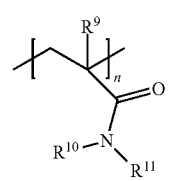

Formula IX where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula X:

Formula X

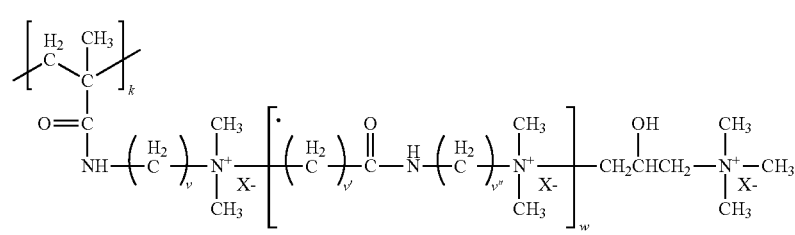

where k =1, each of v, v', and v" is independently an integer of from 1 to 6, w is zero or an integer of from 1 to 10, and X⁻ is an anion.

A cationic monomer can conform to Formula X where k=1, v=3 and w=0, z=1 and X⁻ is Cl⁻ to form the following structure (Formula XI):

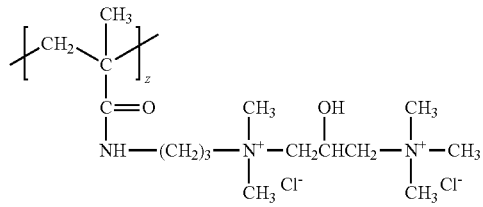

Formula XI

As can be appreciated, the above structure can be referred to as diquat.

A cationic monomer can conform to Formula X wherein v and v" are each 3, v'=1, w=1, y=1 and X⁻ is Cl⁻, to form the following structure of Formula XII:

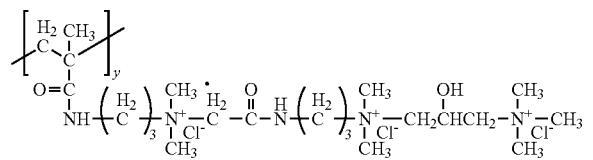

Formula XII

The structure of Formula XII can be referred to as triquat.

The acrylamide monomer can be either acrylamide or methacrylamide.

The cationic copolymer can be AM:TRIQUAT which is a copolymer of acrylamide and 1,3-Propanediaminium, N-[2-[[[dimethyl[3-[(2-methyl-1-oxo-2 -propenyl)amino]propyl]ammonio]acetyl]amino]ethyl]2-hydroxy-N,N,N',N',N'-pentamethyl—, trichloride. AM:TRIQUAT is also known as polyquaternium 76 (PQ76). AM:TRIQUAT can have a charge density of 1.6 meq/g and a M.Wt. of 1.1 million g/mol.

The cationic copolymer can include an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can include a cationic monomer selected from the group consisting of: trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters can be cationized esters of the (meth)acrylic acid containing a quaternized N atom. Cationized esters of the (meth)acrylic acid containing a quaternized N atom are quaternized dialkylaminoalkyl (meth)acrylates with $C_1$ to $C_3$ in the alkyl and alkylene groups. The cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides are quaternized dialkylaminoalkyl(meth)acrylamides with $C_1$ to $C_3$ in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide can be a quaternized dialkylaminoalkyl(meth)acrylamide with $C_1$ to $C_3$ in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, any monomer that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, from about 1.1 meq/g to about 2.3 meq/g, from about 1.2 meq/g to about 2.2 meq/g, from about 1.2 meq/g to about 2.1 meq/g, from about 1.3 meq/g to about 2.0 meq/g, and from about 1.3 meq/g to about 1.9 meq/g.

The cationic copolymer can have a M.Wt. from about 100 thousand g/mol to about 2 million g/mol, from about 300 thousand g/mol to about 1.8 million g/mol, from about 500 thousand g/mol to about 1.6 million g/mol, from about 700 thousand g/mol to about 1.4 million g/mol, and from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC can have a charge density of about 1.3 meq/g and a M.Wt. of about 1.1 million g/mol. The cationic copolymer is AM:ATPAC. AM:ATPAC can have a charge density of about 1.8 meq/g and a M.Wt. of about 1.1 million g/mol.

Synthetic Polymers

A cationic polymer can be a synthetic polymer that is formed from:

i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers which have the structure of Formula XIII:

Formula XIII

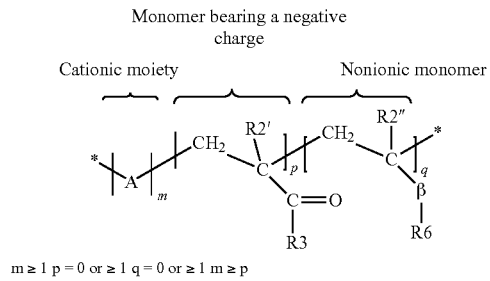

$m \geq 1 \; p = 0 \text{ or } \geq 1 \; q = 0 \text{ or } \geq 1 \; m \geq p$ where A, may be one or more of the following cationic moieties:

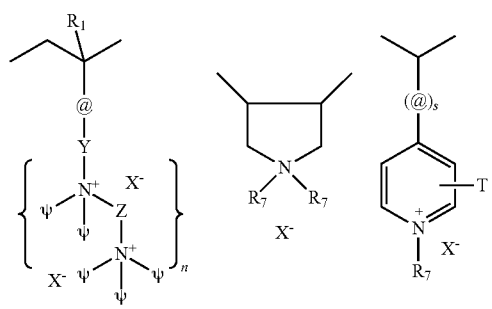

where @ =amido, alkylamido, ester, ether, alkyl or alkylaryl;
where $Y$ =C1-C22 alkyl, alkoxy, alkylidene, alkyl or aryloxy;
where $\Psi$=C1-C22 alkyl, alkyloxy, alkyl aryl or alkyl arylox;.
where $Z$=C1-C22 alkyl, alkyloxy, aryl or aryloxy;
where $R1$=H, C1-C4 linear or branched alkyl;

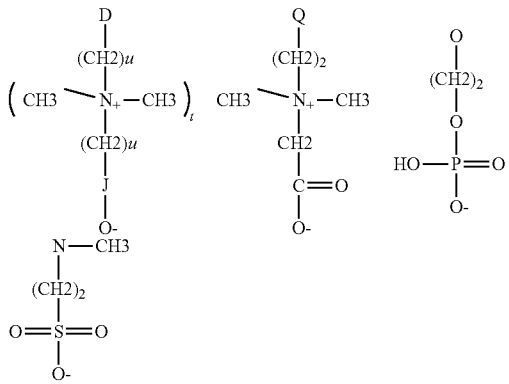

where s=0 or 1, n=0 or $\geq 1$;
where T and R7=C1-C22 alkyl; and
where X—=halogen, hydroxide, alkoxide, sulfate or alkylsulfate.

Where the monomer bearing a negative charge is defined by R2'=H, $C_1$-$C_4$ linear or branched alkyl and R3 is:
where D=O, N, or S;
where Q=$NH_2$ or O;
where u=1-6;
where t=0-1; and
where J=oxygenated functional group containing the following elements P, S, C.

Where the nonionic monomer is defined by R2″=H, $C_1$-$C_4$ linear or branched alkyl, R6=linear or branched alkyl, alkyl aryl, aryl oxy, alkyloxy, alkylaryl oxy and β is defined as

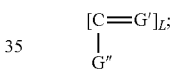

and where G' and G″ are, independently of one another, O, S or N—H and L=0 or 1.

Suitable monomers can include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of suitable cationic monomers can include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers can include quaternary monomers of formula —$NR_3^+$, wherein each R can be identical or different, and can be a hydrogen atom, an alkyl group comprising 1 to 10 carbon atoms, or a benzyl group, optionally carrying a hydroxyl group, and including an anion (counter-ion). Examples of suitable anions include halides such as chlorides, bromides, phosphates, citrates, formates, and acetates.

Suitable cationic monomers can also include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Additional suitable cationic monomers can include trimethyl ammonium propyl (meth) acrylamido chloride.

Examples of monomers bearing a negative charge include alpha ethylenically unsaturated monomers including a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge can include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers can include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers can also include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion ($X^-$) in association with the synthetic cationic polymers can be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non-limiting examples of suitable counterions can include halides (e.g., chlorine, fluorine, bromine, iodine).

The cationic polymer described herein can also aid in repairing damaged hair, particularly chemically treated hair by providing a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer can return the hair to a generally virgin-like, healthier state. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in PCT Patent App. No. WO 94/06403 which is incorporated by reference. The synthetic polymers described herein can be formulated in a stable shampoo composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density is about 6.2 meq/gm. The polymers also have a M. Wt. of from about 1,000 to about 5,000,000, and/or from about 10,000 to about 2,000,000, and/or from about 100,000 to about 2,000,000.

Cationic synthetic polymers that provide enhanced conditioning and deposition of benefit agents but do not necessarily form lytropic liquid crystals can have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M.Wt. of from about 1,000 g/mol to about 5,000,000 g/mol, from about 10,000 g/mol to about 2,000,000 g/mol, and from about 100,000 g/mol to about 2,000,000 g/mol.

Cationic Cellulose Polymer

Suitable cationic polymers can be cellulose polymers. Suitable cellulose polymers can include salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose can include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose can include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference.

Techniques for analysis of formation of complex coacervates are known in the art. For example, microscopic analyses of the compositions, at any chosen stage of dilution, can be utilized to identify whether a coacervate phase has formed. Such coacervate phase can be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164 which is incorporated by reference.

Anti-Dandruff and Scalp Care Actives

Anti-dandruff agents suitable for use in shampoo compositions can include piroctone olamine (commercially available as Octopirox®), pyridinethione salts, azoles (e.g., ketoconazole, econazole, and elubiol), selenium sulfide, particulate sulfur, salicylic acid, zinc pyrithione, and mixtures thereof. The composition can include anti-dandruff agents that are soluble, non-particulate actives such as Piroctone Olamine. Example of scalp care actives can include Hydroxyphenyl Propamidobenzoic Acid available from Symrise as SymCalmin®.

Chelating Agents

The shampoo composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440. U.S. Pat. No. 5,284,972 and U.S. Pat. No. 5,747,440 are each incorporated by reference herein. Suitable chelants can further include histidine.

Levels of an EDDS chelant or histidine chelant in the shampoo compositions can be low. For example, an EDDS chelant or histidine chelant can be included at about 0.01%, by weight. Above about 10% by weight, formulation and/or human safety concerns can arise. The level of an EDDS chelant or histidine chelant can be at least about 0.05%, by weight, at least about 0.1%, by weight, at least about 0.25%, by weight, at least about 0.5%, by weight, at least about 1%, by weight, or at least about 2%, by weight, by weight of the shampoo composition.

Product Form

The shampoo compositions may be presented in typical hair care formulations. They may be in the form of solutions, dispersion, emulsions, foams, and other delivery mechanisms. The composition can be a low viscosity or a viscous liquid that can be applied to wet hair, then massaged into the hair, and then rinsed out.

The shampoo composition in the form of a foam can have a density of from about 0.02 g/cm$^3$ to about 0.2 g/cm$^3$, alternatively from about 0.025 g/cm$^3$ to about 0.15 g/cm$^3$, and alternatively from about 0.05 g/cm$^3$ to about 0.15 g/cm$^3$. The density can be measured Foam Density & Foam Volume Method, described hereafter.

Foam Dispenser

The shampoo composition can be stored and dispensed from an aerosol foam dispenser that can include a reservoir for holding the shampoo composition. The reservoir may be made from any suitable material including materials selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. Alternatively, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

Alternatively, the hair composition can be stored and dispensed from a mechanical foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The shampoo composition can be stored and dispensed from a squeeze foam dispenser. An example of squeeze foamer is EZ'R available from Albéa.

The shampoo composition and/or the dispenser can be free or substantially free of a propellant, for instance aerosol propellants.

Propellant

The shampoo composition described herein may comprise from about from about 2% to about 10% propellant, alternatively from about 3% to about 8% propellant, and alternatively from about 4% to about 7% propellant, by weight of the shampoo.

The propellant may comprise one or more volatile materials, which in a gaseous state, may carry the other components of the shampoo in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the shampoo composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene (HFO 1234ze available by Honeywell), and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The foaming agent may comprise hydrofluoroolefins (HFOs).

Compositions that use an HFO propellant can have a higher foam densities (approximately 2× greater) versus hydrocarbon propellants and at equal formula pressure and formula % saturated pressure. The higher density can enable higher gravimetric foam dosage per unit volume of the resulting dispensed foam shampoo. This means that a consumer could use a smaller volume of foam to achieve similar results when using a less dense foam.

The pressure and % saturated pressure can be important to enable sufficient foam dispensing over the life of the product (from beginning to middle to end of the pressurized container). The 1,3,3,3-tetrafluoropropene can also enable significantly greater gloss or shine of the dispensed foam.

Test Methods

Cone/Plate Viscosity Measurement

The viscosities of the examples are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The liquid viscosity is determined using a steady state flow experiment at constant shear rate of 2000 $s^{-1}$ and at temperature of 26.5° C. The sample size is 2.5 ml and the total measurement reading time is 3 minutes.

Foam Density & Foam Volume

Foam density is measured by placing a 100 ml beaker onto a mass balance, tarring the mass of the beaker and then dispensing product from the aerosol container into the 100 ml beaker until the volume of the foam is above the rim of the vessel. The foam is made level with the top of the beaker by scraping a spatula across it within 10 seconds of dispensing the foam above the rim of the vessel. The resulting mass of the 100 ml of foam is then divided by the volume (100) to determine the foam density in units of g/ml.

Foam volume is measured by placing a weigh boat onto a mass balance, tarring the mass of the weigh boat and then dispensing the desired amount of product from the aerosol container. The grams of foam dispensed is determined and then divided by the density of foam as determined from the Foam Density methodology to reach a volume of foam in ml or $cm^3$.

Light Transmittance

Techniques for analysis of formation of complex coacervates are known in the art. One method to assess coacervate formation upon dilution for a transparent or translucent composition is to use a spectrophotometer to measure the percentage of light transmitted through the diluted sample (% T). As percent light transmittance (% T) values measured of the dilution decrease, typically higher levels of coacervate are formed. Dilutions samples at various weight ratios of water to composition can be prepared, for example 2 parts of water to 1 part composition (2:1), or 7.5 parts of water to 1 part composition (7.5:1), or 16 parts of water to 1 part composition (16:1), or 34 parts of water to 1 part composition (34:1), and the % T measured for each dilution ratio sample. Examples of possible dilution ratios may include 2:1, 3:1, 5:1, 7.5:1, 11:1, 16:1, 24:1, or 34:1. By averaging the % T values for samples that span a range of dilution ratios, it is possible to simulate and ascertain how much coacervate a composition on average would form as a consumer applies the composition to wet hair, lathers, and then rinses it out. Average % T can be calculated by taking the numerical average of individual % T measurements for the following dilution ratios: 2:1, 3:1, 5:1, 7.5:1, 11:1, 16:1, 24:1, and 34:1.

% T can be measured using Ultra-Violet/Visible (UV/VI) spectrophotometry which determines the transmission of UV/VIS light through a sample. A light wavelength of 600 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer to 600 nm. Then a calibration "blank" is run to calibrate the readout to 100 percent transmittance. A single test sample is then placed in a cuvette designed to fit the specific spectrophotometer and care is taken to insure no air bubbles are within the sample before the % T is measured by the spectrophotometer at 600 nm. Alternatively, multiple samples can be measured simultaneously by using a spectrophotometer such as the SpectraMax M-5 available from Molecular Devices. Multiple dilution samples can be prepared within a 96 well plate (VWR catalog #82006-448) and then transferred to a 96 well visible flat bottom plate (Greiner part #655-001), ensuring that no air bubbles are within the sample. The flat bottom plate is placed within the SpectraMax M-5 and % T measured using the Software Pro v.5™ software available from Molecular Devices.

EXAMPLES

The following are non-limiting examples of the shampoo composition described herein. The examples were prepared by conventional techniques and included adding the ingredients one by one and mixing until homogeneous or dissolved and adding heat as necessary to dissolve particular ingredients. It will be appreciated that other modifications of the present invention within the skill of those in the shampoo formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

TABLE 1

Comparative Examples 1-5 of Compact Shampoo Compositions

|  | Comp. Ex. 1 | Comp. Ex. 2 | Comp. Ex. 3 | Comp. Ex. 4 | Comp. Ex. 5 |
|---|---|---|---|---|---|
| Disodium cocoyl glutamate[1] | 15 | 15 | 15 | 15 | 15 |
| Sodium cocoyl isethionate[2] | 5 | 5 | 5 | 5 | 5 |
| Lauramidopropyl betaine[3] | — | — | 3 | 5 | — |
| Cocamidopropyl betaine[4] | — | 1 | — | — | 5 |
| Sodium lauroamphoacetate[5] | — | — | — | — | — |
| Polyquaternium-6[6] | 0.2 | 0.2 | 0.2 | 0.2 | 0.2 |
| Versene ™ 220[7] | 0.16 | 0.16 | 0.16 | 0.17 | 0.16 |

TABLE 1-continued

Comparative Examples 1-5 of Compact Shampoo Compositions

| | Comp. Ex. 1 | Comp. Ex. 2 | Comp. Ex. 3 | Comp. Ex. 4 | Comp. Ex. 5 |
|---|---|---|---|---|---|
| Natrlquest E30[8] | 0.23 | 0.23 | 0.23 | 0.23 | 0.23 |
| Sodium benzoate[9] | 0.24 | 0.24 | 0.24 | 0.24 | 0.24 |
| Kathon ™[10] | 0.03 | 0.03 | 0.03 | 0.03 | 0.03 |
| Perfume | 0.90 | 0.90 | 0.90 | 0.90 | 0.90 |
| DL-Panthanol 50L[11] | 0.05 | 0.05 | 0.05 | 0.05 | 0.05 |
| D/DI Panthenyl ether[12] | 0.03 | 0.03 | 0.03 | 0.03 | 0.03 |
| Citric acid | To pH 6.0 | To pH 6.0 | To pH 6.0 | To pH 6.0 | To pH 6.0 |
| Water | Q.S. | Q.S. | Q.S. | Q.S. | Q.S. |
| Weight ratio zwitterionic co-surfactant/sodium cocoyl isethionate | 0 | 0.2 | 0.6 | 1.0 | 1.0 |
| Appearance at ambient temperature (20-25° C.) | Clear | Clear | Clear | Clear | Clear |
| Appearance at 5° C. | Cloudy | Cloudy | Cloudy | Cloudy | Cloudy |

TABLE 2

Comparative Examples 6-9 of Compact Shampoo Compositions

| | Comp. Ex. 6 | Comp. Ex. 7 | Comp. Ex. 8 | Comp. Ex. 9 |
|---|---|---|---|---|
| Disodium cocoyl glutamate[1] | 20 | 20 | 20 | 20 |
| Sodium cocoyl isethionate[2] | 5 | 5 | 5 | 5 |
| Lauramidopropyl betaine[3] | — | 5 | — | 5 |
| Cocamidopropyl betaine[4] | — | — | 5 | — |
| Sodium lauroamphoacetate[5] | 5 | — | — | — |
| Polyquaternium-6[6] | 0.2 | 0.2 | 0.2 | — |
| Versene ™ 220[7] | 0.16 | 0.16 | 0.16 | 0.17 |
| Natrlquest E30[8] | 0.23 | 0.23 | 0.23 | 0.23 |
| Sodium benzoate[9] | 0.24 | 0.24 | 0.24 | 0.24 |
| Kathon ™[10] | 0.03 | 0.03 | 0.03 | 0.03 |
| Perfume | 0.90 | 0.90 | 0.90 | 0.90 |
| DL-Panthanol 50L[11] | 0.05 | 0.05 | 0.05 | 0.05 |
| D/DI Panthenyl ether[12] | 0.03 | 0.03 | 0.03 | 0.03 |
| Citric acid | To pH 6.0 | To pH 6.0 | To pH 6.0 | To pH 6.0 |
| Water | Q.S. | Q.S. | Q.S. | Q.S. |
| Weight ratio zwitterionic co-surfactant/sodium cocoyl isethionate | 1.0 | 1.0 | 1.0 | 1.0 |
| Appearance at ambient temperature (20-25° C.) | Clear | Clear | Clear | Clear |
| Appearance at 5° C. | Cloudy | Cloudy | Cloudy | Cloudy |

TABLE 3

Examples A-F of Compact Shampoo Compositions

| | Ex. A | Ex. B | Ex. C | Ex. D | Ex. E | Ex. F |
|---|---|---|---|---|---|---|
| Disodium cocoyl glutamate[1] | 15 | 15 | 15 | 10 | — | 5 |
| Sodium Laureth Sulfosuccinate[13] | — | — | — | — | 10 | — |
| Sodium cocoyl isethionate[2] | 5 | 5 | 5 | 3 | 5 | 3 |
| Lauramidopropyl betaine[3] | 10 | — | 8 | 7 | 10 | — |
| Cocamidopropyl betaine[4] | — | 10 | 0 | — | — | 7 |
| Polyquaternium-6[6] | 0.2 | 0.1 | 0.2 | 0.2 | 0.2 | 0.2 |
| Versene ™ 220[7] | 0.16 | 0.16 | 0.16 | 0.17 | 0.17 | 0.17 |
| Natrlquest E30[8] | 0.23 | 0.23 | 0.23 | 0.23 | 0.23 | 0.23 |
| Sodium benzoate[9] | 0.24 | 0.24 | 0.24 | 0.24 | 0.24 | 0.24 |
| Kathon ™[10] | 0.03 | 0.03 | 0.03 | 0.03 | 0.03 | 0.03 |
| Perfume | 0.90 | 0.90 | 0.90 | 0.90 | 0.90 | 0.90 |
| DL-Panthanol 50L[11] | 0.05 | 0.05 | 0.05 | 0.05 | 0.05 | 0.05 |
| D/DI Panthenyl ether[12] | 0.03 | 0.03 | 0.03 | 0.03 | 0.03 | 0.03 |
| Citric acid | To pH 6.0 | To pH 6.0 | To pH 6.0 | To pH 6.0 | To pH 6.0 | To pH 6.0 |
| Water | Q.S. | Q.S. | Q.S. | Q.S. | Q.S. | Q.S. |

TABLE 3-continued

Examples A-F of Compact Shampoo Compositions

|  | Ex. A | Ex. B | Ex. C | Ex. D | Ex. E | Ex. F |
|---|---|---|---|---|---|---|
| Weight ratio zwitterionic co-surfactant/sodium cocoyl isethionate | 2.0 | 2.0 | 1.6 | 2.3 | 2.0 | 2.3 |
| Appearance at ambient temperature (20-25° C.) | Clear | Clear | Clear | Clear | Clear | Clear |
| Appearance at 5° C. | Clear | Clear | Clear | Clear | Clear | Clear |

1. Disodium cocoyl glutamate, tradename: Eversoft™ UCS-50SG, 40% active from Sino-Lion
2. Sodium cocoyl isethionate, Jordan C Prill from BASF
3. Lauramidopropyl betaine, Mackam® DAB, 35.0% active from Solvay
4. Cocamidopropyl betaine, Amphosol HCA from Stepan
5. Sodium lauroamphoacetate, from BASF
6. Polyquaternium 6, PolyDADMAC, MW of 150,000, CD of 6.2, tradename: Mirapol® 100 s, 31.5% active, from Solvay
7. Versene™ 220, Tetrasodium ethylenediaminetetraacetate tetrahydrate from Dow
8. Natrlquest E30, Trisodium Ethylenediamine Disuccinate, from Innospec.
9. Sodium benzoate from Emerald Kalama Chemical
10. Kathon™CG, Methyl chloro isothiazolinone and Methyl isothiazolinone from Dow
11. DL-Panthanol 50 L from DSM Nutritional Products
12. D/DI Panthenyl ether from DSM Nutritional Products
13. Mackanate EL P from Solvay For Table 1, Table 2, and Table 3 the appearance at ambient (20-25° C.) and appearance at 5° C. was determined as follows. The example was put in a clear, glass jar. The cap was screwed on the jar, finger-tight. The example was stored at ambient temperatures (20-25° C.), away from direct sunlight, for 14 days. Then the example was visually inspected to determine if it was clear and/or phase stable. Next, the example was stored at 5° C. for 24 hours. Then the product was visually inspected to determine if it was clear and/or phase stable after being stored at a cool temperature.

The example was phase stable if by visual detection there is no phase separation, which includes precipitates, and the example appears homogeneous. The example was considered clear if by visual detection if there are no visible particulates and it allows light to pass through so that objects behind can be distinctly seen, similar to water. On the other hand, the example was cloudy if by visual detection the example appeared to have visible material in suspension. As used herein, "visual detection" means that a human viewer can visually discern the quality of the example with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of 1 meter.

Examples A-F could be preferred by consumers over Comparative Examples 1-9 because they are stable and clear at ambient temperature and at 5° C. Comparative Examples 1-9 contain from 20% to 30% total surfactant, which includes from 15% to 20% disodium cocoyl glutamate, 5% sodium cocoyl isethionate, and from 0% to 5% zwitterionic co-surfactant. Comparative Example 1 was clear at ambient temperature and Examples 2-9 were cloudy at ambient temperature. However, Comparative Examples 1-9 all turned cloudy at 5° C., a temperature that may be frequently encountered during shipping, handling, and storage of shampoo compositions.

The Figure shows an example of a cloudy composition 2. Cloudy composition 2 is not consumer preferred and a cloudy shampoo composition may signal to a consumer that the product is ineffective. Furthermore, the cloudy solution can contain small, suspended crystals. Over time, the crystals can agglomerate and form large crystals, which can settle out of solution and be difficult for a consumer to re-suspend, cause non-uniform product usage and/or varying performance throughout the life of the product and/or clog the orifice of the dispenser, particularly an aerosol dispenser.

Examples A-F contain from 15% to 30% total surfactant, which includes 5-15% disodium cocoyl glutamate, 10% sodium sulfosuccinate, 3% to 5% sodium cocoyl isethionate, and 7% to 10% zwitterionic surfactant. Unlike Comparative Examples 1-9, Examples A-F are clear at ambient temperature and there is no change in the appearance when the composition is at 5° C. Examples A-F are single phase compositions at ambient temperature and 5° C. The Figure shows an example of a clear composition 1.

It was surprisingly found the weight ratio of zwitterionic surfactant to sodium cocoyl isethionate is important for phase stability and clarity. Examples A-F, which are single phase and clear, have a weight ratio of zwitterionic surfactant to sodium cocoyl isethionate of 1.6 to about 2.3. Examples, 1-9, which are cloudy when stored at 5° C., have a weight ratio of zwitterionic surfactant to sodium cocoyl isethionate of from 0 to 1.

Combinations

A. A compact shampoo composition comprising:
 a. from about 10% to about 50%, by weight of the composition, of a surfactant system wherein the surfactant system comprises:
  i. from about 5% to about 20%, by weight of the composition, of an anionic surfactant selecting from the group consisting of acyl glutamate, acyl alaninate, acyl glycinate, acyl sarcosinate, sulfonate, carboxylate, sulfosuccinate, taurate or a mixture thereof;
  ii. from about 2% to about 8% sodium cocoyl isethionate;
  iii. from about 5% to about 12% zwitterionic surfactant;
   wherein the ratio of zwitterionic surfactant to sodium cocoyl isethionate is greater than 1.5;
   wherein the composition is clear and stable after storage at ambient temperature and at 5° C.

B. A compact shampoo composition comprising:
  a. from about 20% to about 35%, by weight of the composition, of a surfactant system wherein the surfactant system comprises:
    i. from about 10% to about 20%, by weight of the composition, of an anionic surfactant selecting from the group consisting of acyl glutamate, acyl alaninate, acyl glycinate, acyl sarcosinate, sulfonate, carboxylate, sulfosuccinate, taurate or a mixture thereof;
    ii. from about 2% to about 6% sodium cocoyl isethionate;
    iii. from about 7% to about 10% zwitterionic surfactant;
      wherein the ratio of zwitterionic surfactant to sodium cocol isethionate is from about 1.5 to about 2.5;
      wherein the composition is clear and stable after storage at ambient temperature and at 5° C.

C. The compact shampoo composition according to Paragraphs A-B, comprising from about 15% to about 48%, by weight, surfactant system, preferably from about 18% to about 45%, by weight, more preferably from about 20% to about 40%, by weight, and most preferably from about 22% to about 38%.

D. The compact shampoo composition according to Paragraphs A-C, comprising from about 23% to about 35%, by weight, surfactant system and preferably from about 25% to about 30%.

E. The compact shampoo composition according to Paragraphs A-D, wherein the composition comprises from about 5% to about 40%, by weight of the composition, total anionic surfactant, preferably from about 8% to about 35%, by weight, and more preferably from about 10% to about 30%, by weight of the composition.

F. The compact shampoo composition according to Paragraphs A-E, wherein the composition comprises from about 13% to about 25%, by weight, total anionic surfactant, preferably from about 15% to about 23%, by weight, more preferably from about 17% to about 21%, and even more preferably from about 18% to about 20%.

G. The compact shampoo composition according to Paragraphs A-F, wherein the composition comprises an acyl glutamate level from about 2% to about 25%, by weight, preferably from about 5% to about 20%, by weight, more preferably 10% to about 18%, by weight, and even more preferably from about 12% to about 15%, by weight.

H. The compact shampoo composition according to Paragraphs A-G, wherein the composition comprises less than 20%, by weight, acyl glutamate, preferably less than 18%, by weight, more preferably less than 16%, by weight, and even more preferably less than 15%.

I. The compact shampoo composition according to Paragraphs A-H, wherein the ratio of acyl glutamate to total surfactant can be less than 0.6, preferably less than 0.56, more preferably less than 0.53, and even more preferably less than or equal to 0.51.

J. The compact shampoo composition according to Paragraphs A-I, wherein the ratio of acyl glutamate to total surfactant is from about 0.1 to about 0.58, preferably from about 0.15 to about 0.55, more preferably from about 0.20 to about 0.53, and even more preferably from about 0.25 to about 0.5.

K. The compact shampoo composition according to Paragraphs A-J, wherein the weight ratio of primary surfactant to sodium cocoyl isethionate is from about 1:1 to about 10:1, preferably from about 3:2 to about 7:1, and more preferably from about 3:1 to about 5:1.

L. The compact shampoo composition according to Paragraphs A-K, wherein the weight ratio of primary surfactant to sodium cocoyl isethionate is less than 5:1.

M. The compact shampoo composition according to Paragraphs A-L, wherein the composition comprises a zwitterionic surfactant level from about 1% to about 20%, by weight, preferably from about 5% to about 15%, by weight, more preferably from about 6% to about 12%, by weight, and even more preferably from about 7% to about 12%, by weight.

N. The compact shampoo composition according to Paragraphs A-M, wherein the surfactant system comprises from about 15% to about 40% zwitterionic surfactant, by weight of the surfactant system, preferably from about 22% to about 37%, by weight of the surfactant system, and more preferably from about 25% to about 35%, by weight of the surfactant system.

O. The compact shampoo composition according to Paragraphs A-N, wherein the surfactant system comprises a weight ratio of anionic surfactant to zwitterionic surfactant from about 1:2 to about 5:1, preferably from about 1:1 to about 7:2, more preferably from about 3:2 to about 3:1, and even more preferably from about 2:1 to about 5:2.

P. The compact shampoo composition according to Paragraphs A-O, wherein the surfactant system comprises a weight ratio of anionic surfactant to zwitterionic surfactant of less than 4:1, preferably less than 3:1, and more preferably less than or equal to 5:2.

Q. The compact shampoo composition according to Paragraphs A-P, wherein the surfactant system comprises a weight ratio of zwitterionic surfactant to sodium cocoyl isethionate of from about 1:1 to about 5:1, preferably from about 5:4 to about 4:1, more preferably from about 3:2: to about 3:1, and even more preferably from about 3:2 to about 5:2.

R. The compact shampoo composition according to Paragraphs A-R, wherein the surfactant system comprises a weight ratio of zwitterionic surfactant to sodium cocoyl isethionate greater than 1:1, preferably greater than 5:4, and more preferably greater than 3:2.

S. The compact shampoo composition according to Paragraphs A-R, wherein the composition further comprises a cataionic polymer selected from the group consisting of cationic guar polymers, cationic non-guar galactomannan polymers, cationic starch polymers, cationic copolymer of acrylamide monomers and cationic monomers, synthetic, non-crosslinked cationic polymers, and combinations thereof.

T. The compact shampoo composition according to Paragraph S, wherein the composition comprises from about 0.01% to about 2%, by weight, cationic polymer, preferably from about 0.05% to about 1%, by weight, more preferably from about 0.1% to about 0.8%, by weight, and even more preferably from about 0.1% to about 0.5%, by weight.

U. The compact shampoo composition according to Paragraphs A-T, wherein the composition further comprises from about 50% to about 95%, by weight of the composition, liquid carrier, preferably about 60% to about 85%, by weight of the composition, and more preferably from about 65% to about 80%.

V. The compact shampoo composition according to Paragraphs A-U, wherein the composition further comprises a liquid carrier and wherein the liquid carrier comprises water.

W. The compact shampoo composition according to Paragraphs A-V, wherein the acyl glutamate comprises disodium cocoyl glutamate.

X. The compact shampoo composition according to Paragraphs A-W, the zwitterionic surfactant is selected from the group consisting of cocamidopropyl betaine (CAPB), lauramidopropyl betaine (LAPB), and combinations thereof.

Y. The compact shampoo composition according to Paragraphs A-X, wherein the composition comprises from about 0.05% to about 1%, by weight of the composition, cationic polymer more preferably from about 0.1% to about 0.8%, by weight, and even more preferably from 0.1% to about 0.5%, by weight.

Z. The compact shampoo composition according to Paragraphs A-Y, wherein the shampoo composition comprises a viscosity from about 1 cP to about 5000 cP, preferably from about 2 cP to about 3000 cP, more preferably from about 5 cP to about 2000 cP, and even more preferably from about 10 cP to about 1000 cP, at temperature of 26.5° C., as determined by the Cone/Plate Viscosity Measurement, described herein.

AA. The compact shampoo composition according to Paragraphs A-Z, wherein the shampoo composition comprises a viscosity alternatively from about 10 cP to about 500 cP, and more preferably from about 20 cP about 100 cP, at constant shear rate of 2000 $s^{-1}$, at temperature of 26.5° C., as determined by the Cone/Plate Viscosity Measurement, described herein.

BB. The compact shampoo composition according to Paragraphs A-AA, wherein the composition comprises a viscosity less than 100 cP, preferably less than 60 cP, more preferably less than 40 cP, and even more preferably less than 30 cP, at temperature of 26.5° C., as determined by the Cone/Plate Viscosity Measurement, described herein.

CC. The compact shampoo composition according to Paragraphs A-BB, wherein the shampoo composition is substantially free of a viscosity reducing agent selected from the group consisting of propylene glycol, dipropylene glycol, alcohols, glycerin, and combinations thereof.

DD. The compact shampoo composition according to Paragraphs A-CC, wherein the shampoo composition is substantially free of a thickeners selected from the group consisting of acrylate polymers and co-polymers, xanthan gum, and combinations thereof.

EE. The compact shampoo composition according to Paragraphs A-DD, wherein the shampoo composition comprises a pH from about 2 to about 10, preferably from about 4 to about 8, and more preferably from about from about 5 to about 7.

FF. The compact shampoo composition according to Paragraphs A-EE, wherein the shampoo composition further comprises a conditioning agent selected from the group consisting of silicone conditioning agents, organic conditioning materials, and combinations thereof.

GG. The compact shampoo composition according to Paragraphs A-FF, wherein the shampoo composition further comprises an anti-dandruff active selected from the group consisting of piroctone olamine, pyridinethione salts, azoles (e.g.,ketoconazole, econazole, and elubiol), selenium sulfide, particulate sulfur, salicylic acid, zinc pyrithione, and mixtures thereof.

HH. A method of treating hair, the method comprising:
  a. applying to the hair the stable shampoo composition according to Paragraphs A-GG, wherein the shampoo composition is dispensed from an aerosol foam dispenser or a pump foam dispenser as a dosage of foam;
  b. rinsing the hair care composition;
  c. optionally applying got the hair a second hair care composition.

II. The method of Paragraph HH, wherein the shampoo composition is dispensed from an aerosol dispenser as a foam and wherein the shampoo composition further comprises from about 2% to about 10%, by weight of the composition, propellant, preferably from about 3% to about 8%, by weight of the composition, propellant, and more preferably from about 4% to about 7%, by weight of the composition, propellant.

JJ. The method of Paragraph II, wherein the propellant is selected from the group consisting of propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1 -difluoroethylene, 1,1-difluoroethane, dimethyl ether, monochlorodifluoromethane, trans-1,3,3,3-tetrafluoropropene (HFO 1234ze available by Honeywell), and combinations thereof.

KK. The method of Paragraph II, wherein the propellant comprises trans-1,3,3,3-tetrafluoropropene.

LL. The method of Paragraphs II-KK, wherein the foam has a density of from about 0.02 $g/cm^3$ to about 0.2 $g/cm^3$, preferably from about 0.025 $g/cm^3$ to about 0.15 $g/cm^3$, and a more preferably from about 0.05 $g/cm^3$ to about 0.15 $g/cm^3$.

MM. Use of a weight ratio weight ratio of zwitterionic surfactant to sodium cocoyl isethionate greater than 1.5 to stabilize the shampoo composition of Paragraphs A-LL.

NN. The dosage of foam wherein the foam comprises the shampoo composition of Paragraphs A-MM.

OO. The dosage of foam of Paragraph NN wherein the dosage of foam comprises a volume of from about 5 $cm^3$ to about 150 $cm^3$, preferably from about 15 $cm^3$ to about 150 $cm^3$, and more preferably about 30 $cm^3$ to about 150 $cm^3$.

PP. The dosage of foam of Paragraph KK wherein the dosage of foam comprises a volume of from about 5 $cm^3$ to about 90 $cm^3$, preferably from about 20 $cm^3$ to about 70 $cm^3$, and more preferably from about 30 $cm^3$ to about 70 $cm^3$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating hair, the method comprising:
   a. providing an aerosol foam dispenser comprising a reservoir containing a propellant and a compact shampoo composition comprising:
      i. from about 23% to about 35%, by weight of the composition, of a surfactant system wherein the surfactant system comprises:
         1. from about 10% to about 18%, by weight of the composition, of a primary anionic surfactant consisting of acyl glutamate;
         2. from about 2% to about 6% sodium cocoyl isethionate;
         3. from about 7% to about 10% zwitterionic surfactant selected from the group consisting of cocamidopropyl betaine (CAPB), lauramidopropyl betaine (LAPB), coco-betaine, lauryl hydroxysultaine, cocamidopropyl hydroxysultaine and combinations thereof;
         wherein the ratio of zwitterionic surfactant to sodium cocoyl isethionate is from about 1.5 to about 2.5;
         wherein the composition is clear and phase stable after storage at 20-25° C. for 14 days and at 5° C. for 24 hours;
         wherein the shampoo composition is substantially free of sulfate-based surfactants;
         wherein the shampoo composition comprises a viscosity from about 2 cP to about 3000 cP
   b. dispensing the compact shampoo composition from the aerosol foam dispenser as a dosage of foam;
   c. applying to the hair the dosage of foam;
   d. rinsing the dosage of foam from the hair.

2. The method of claim 1, wherein the propellant is selected from the group consisting of propane, n-butane, isobutane, cyclopropane, dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and combinations thereof.

3. The method of claim 2, wherein the propellant comprises trans-1,3,3,3- tetrafluoropropene.

4. The method of claim 1, wherein the foam has a density of from about 0.02 g/cm$^3$ to about 0.2 g/cm$^3$.

5. The method of claim 1, wherein the shampoo composition is substantially free of a viscosity reducing agent selected from the group consisting of propylene glycol, dipropylene glycol, alcohols, glycerin, and combinations thereof.

6. The method of claim 1, wherein the acyl glutamate comprises disodium cocoyl glutamate.

7. The method of claim 1, wherein the shampoo composition further comprises a conditioning agent selected from the group consisting of silicone conditioning agents, organic conditioning materials, and combinations thereof.

8. The method of claim 1, wherein the shampoo composition further comprises an anti-dandruff active selected from the group consisting of piroctone olamine, pyridinethione salts, azoles, selenium sulfide, particulate sulfur, salicylic acid, zinc pyrithione, and mixtures thereof.

9. The method of claim 1, wherein the shampoo composition is substantially free of one or more thickeners selected from the group consisting of acrylate polymers and copolymers, xanthan gum, and combinations thereof.

* * * * *